US010166302B2

(12) United States Patent
Kim et al.

(10) Patent No.: US 10,166,302 B2
(45) Date of Patent: Jan. 1, 2019

(54) LABELING COMPOSITION FOR CANCER LESION

(71) Applicant: NATIONAL CANCER CENTER, Gyeonggi-do (KR)

(72) Inventors: Seok Ki Kim, Seoul (KR); Se Hun Kang, Gyeonggi-do (KR); Seok Won Kim, Seoul (KR); So Youn Jung, Gyeonggi-do (KR)

(73) Assignee: NATIONAL CANCER CENTER, Gyeonggo-do (KR)

( * ) Notice: Subject to any disclaimer, the term of this patent is extended or adjusted under 35 U.S.C. 154(b) by 78 days.

(21) Appl. No.: 14/758,179

(22) PCT Filed: Dec. 4, 2013

(86) PCT No.: PCT/KR2013/011177
§ 371 (c)(1),
(2) Date: Jun. 26, 2015

(87) PCT Pub. No.: WO2014/104605
PCT Pub. Date: Jul. 3, 2014

(65) Prior Publication Data
US 2015/0328345 A1 Nov. 19, 2015

(30) Foreign Application Priority Data
Dec. 26, 2012 (KR) .................. 10-2012-0153793

(51) Int. Cl.
*A61K 51/00* (2006.01)
*A61M 36/14* (2006.01)
*A61K 51/08* (2006.01)
*A61K 49/00* (2006.01)
*G01N 33/58* (2006.01)
*G01N 33/574* (2006.01)

(52) U.S. Cl.
CPC .......... *A61K 51/081* (2013.01); *A61K 49/006* (2013.01); *A61K 49/0056* (2013.01); *G01N 33/574* (2013.01); *G01N 33/58* (2013.01); *G01N 2333/765* (2013.01)

(58) Field of Classification Search
CPC ..... A61K 51/081; A61K 49/006; G01N 33/58
USPC ....................................................... 424/1.69
See application file for complete search history.

(56) References Cited

U.S. PATENT DOCUMENTS 4,094,965 A 6/1978 Layne et al.
2007/0098724 A1* 5/2007 Noujaim et al. ........... 424/145.1

FOREIGN PATENT DOCUMENTS

| EP | 2 471 557 A1 | 7/2012 |
| KR | 1020110135833 A | 12/2011 |
| KR | 1020120015849 A | * 2/2012 |
| KR | 1020120015849 A | 2/2012 |
| WO | 98/43680 A1 | 10/1998 |
| WO | 00/74727 A2 | 12/2000 |
| WO | WO 0074727 A2 | * 12/2000 |
| WO | 2009/116556 A1 | 9/2009 |

OTHER PUBLICATIONS

Bertoni et al. Biotechnol. Lett (2006) 28: 697-702.*
Liu et al. Biomaterials 208 (2007)3236-3244.*
De Cicco et al. Q. J. Nuc. Med. 2002, 46, 145-152.*
Young et al. J. Control Rel. 2005, 109, 256-274.*
Lovrics et al. EJSO 2011, 37, 388-397.*
Masao Kaneko, M.D., Tsuneo Sasaki, M.D. and Choichiro Kido, M.D., "Positive Scientigraphy of Tumor by Means of Intra-Arterial Injection of Radio-Iodinated Macroaggregated Albumin (MAA)", vol. 102, No. I, p. 81-82, the Department of Diagnostic Radiology, Aichi Cancer Center Hospital, Nagoya, Japan.
A. Martino et al., "A New Radioguided Procedure for Localization and Surgical Treatment of Neck Node Metastasis of Papillary Thyroid Cancer", Journal of Endocrinological Investigation, vol. 33, No. 5, pp. 339-342, May 2010.
Patrick Flamen et al., "Multimodality imaging can predict the metabolic response of unresectable colorectal liver metastases to radioemboliztion therapy with Yttrium-90 labeled resin microspheres", Physics in medicine and biology, Institute of Physics Publishing, Bristol GB, vol. 53, No. 22, pp. 6591-6603, Nov. 21, 2008.
D. Sarlos et al., "Radioguided occult lesion localiztion (ROLL) for treatment and diagnosis of malignant and premalignant breast lesions combined with sentinel node biopsy: A prospective clinical trial with 100 patients", European Journal of Surgical Oncology, London, GB, vol. 35, No. 4, pp. 403-408, Apr. 1, 2009.
Daniel M. Jones et al., "Diagnosis of intra cardiac thrombus by technetium-99M labeled macro aggregated albumin scinti scanning", Radiology, Radiological Society of North America, Inc. US, vol. 122, No. 1, pp. 175-176, Jan. 1, 1977.
Supplementary European Search Report issued in EP Application No. 13866879.3 (national phase application of PCT/KR2013/011177), dated Jun. 15, 2016, total 9 pages.

(Continued)

*Primary Examiner* — Michael G Hartley
*Assistant Examiner* — Sean R Donohue
(74) *Attorney, Agent, or Firm* — Masuvalley & Partners

(57) ABSTRACT

The present invention relates to a labeling composition for a cancer lesion, having a complex in which a pigment for straining living tissues, a radioactive isotope, or a combination thereof binds to macro aggregated albumin (MAA). A method for providing information regarding a cancer lesion site using the labeling composition for a cancer lesion. A labeling kit for a cancer lesion having the labeling composition for a cancer lesion; and a complex in which a pigment for straining living tissues binds to MAA included in the labeling composition for a cancer lesion. The labeling composition for a cancer lesion according to the present invention binds to a cancer lesion to detect a site, size, and the like of the cancer lesion in real time, thereby improving the success rate of a surgical operation for the cancer lesion and also preventing excessive loss of normal tissues.

13 Claims, 10 Drawing Sheets

(56) References Cited

OTHER PUBLICATIONS

Bakheet Elsadek et al., "Impact of albumin on drug delivery—New applications on the horizon", Elsevier, Journal of Controlled Release, vol. 157, pp. 4-28, available online Sep. 16, 2011, www.elsevier.com/locate/iconrel.

Toshiaki Tanaka et al., "An Experimental Study on Antitumor Effect of MMC-Fibrin Glue Mixture", Jpn Cancer Chemother, vol. 23, No. 11, pp. 1400-1402, Sep. 1996.

Tetsuaki Kubota et al., "Local Chemotherapy by a Sustained-Releas882, e Preparation With Fibrin Seal Against the Operative Wound in Head and Neck Cancer", Jpn vol. 22, No. 7, pp. 877-882, Jun. 1995.

\* cited by examiner

[Figure 1]
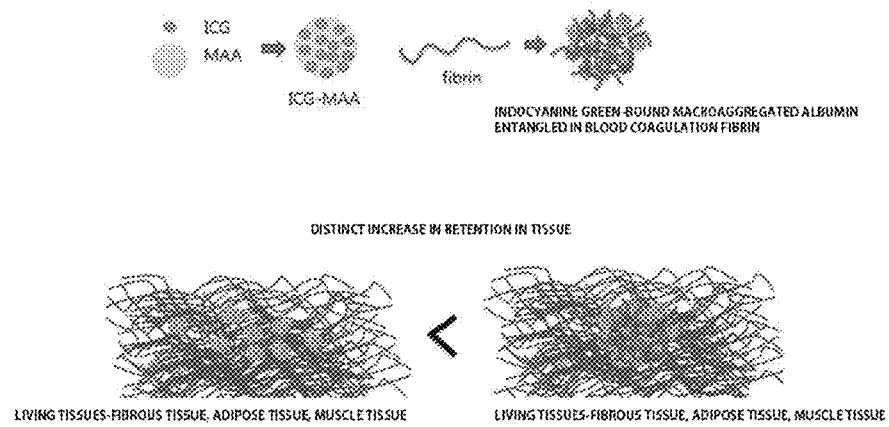
[Figure 2]
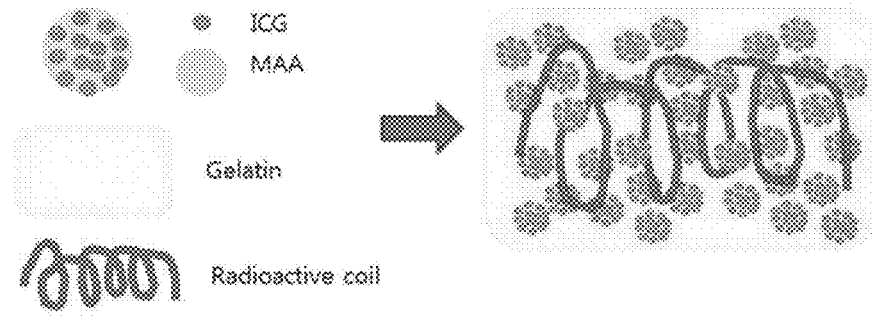
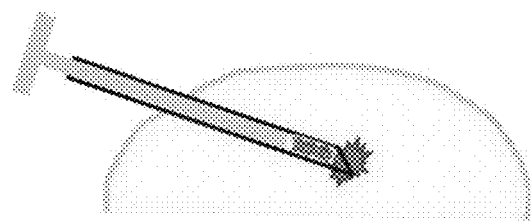

【Figure 3】
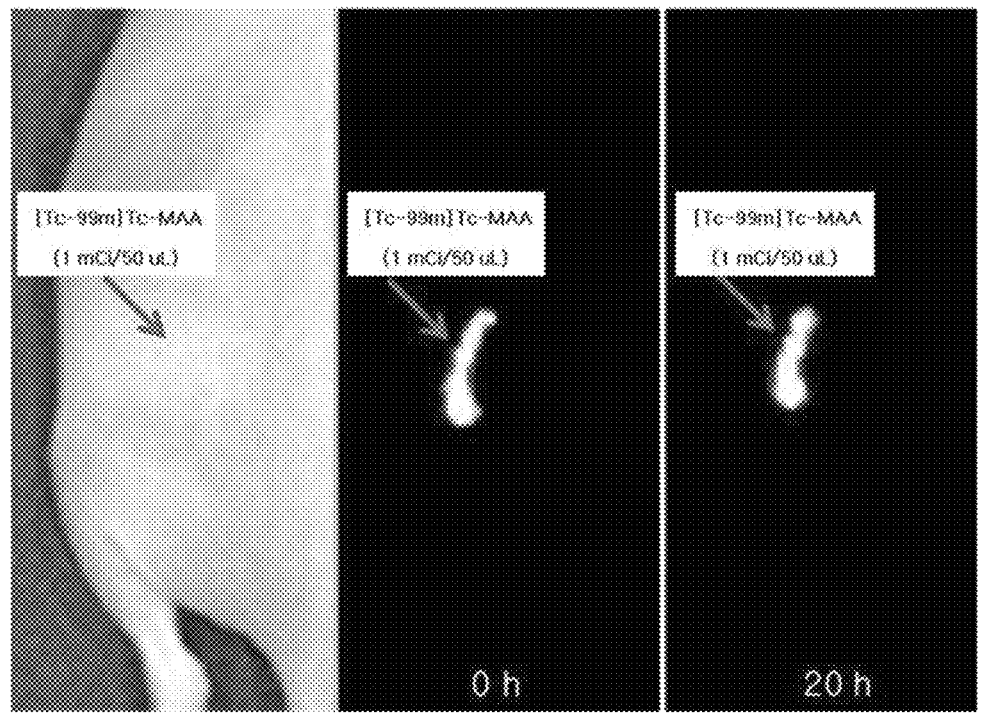
【Figure 4】
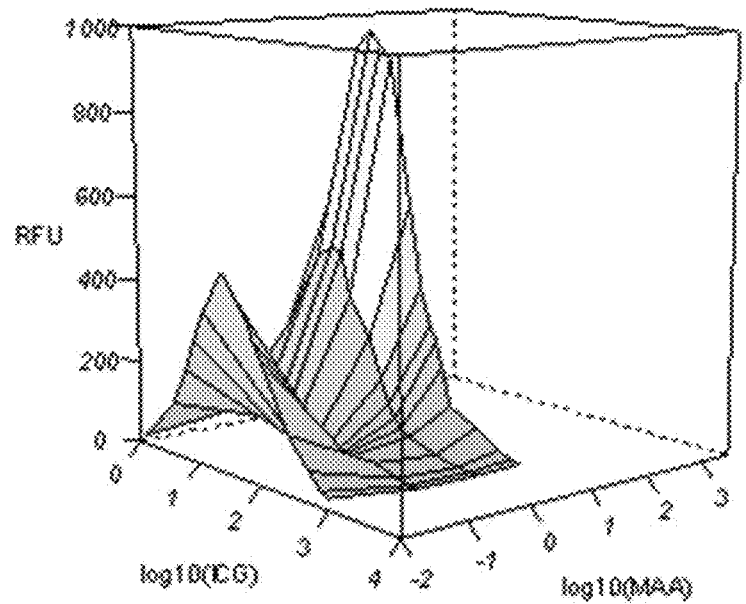

[Figure 5]
COMPARISON OF STABILITY OF NEAR-INFRARED FLUORESCENCE OF ICG-LABELING AGENT COMPLEXES
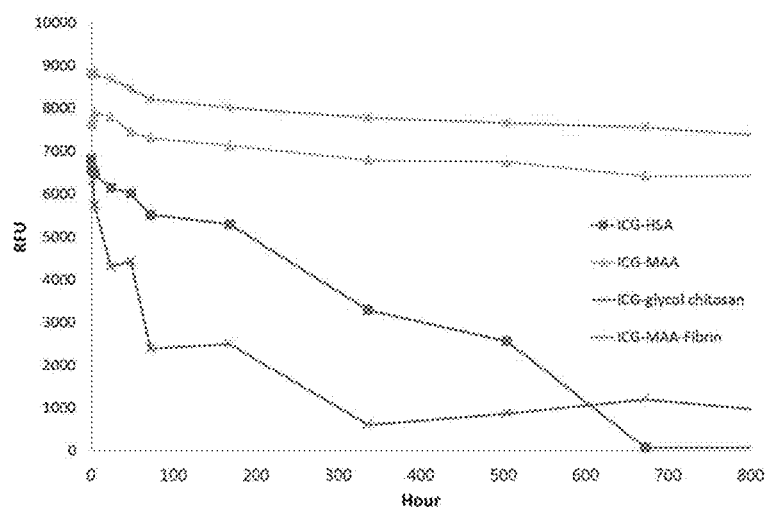

[Figure 6]
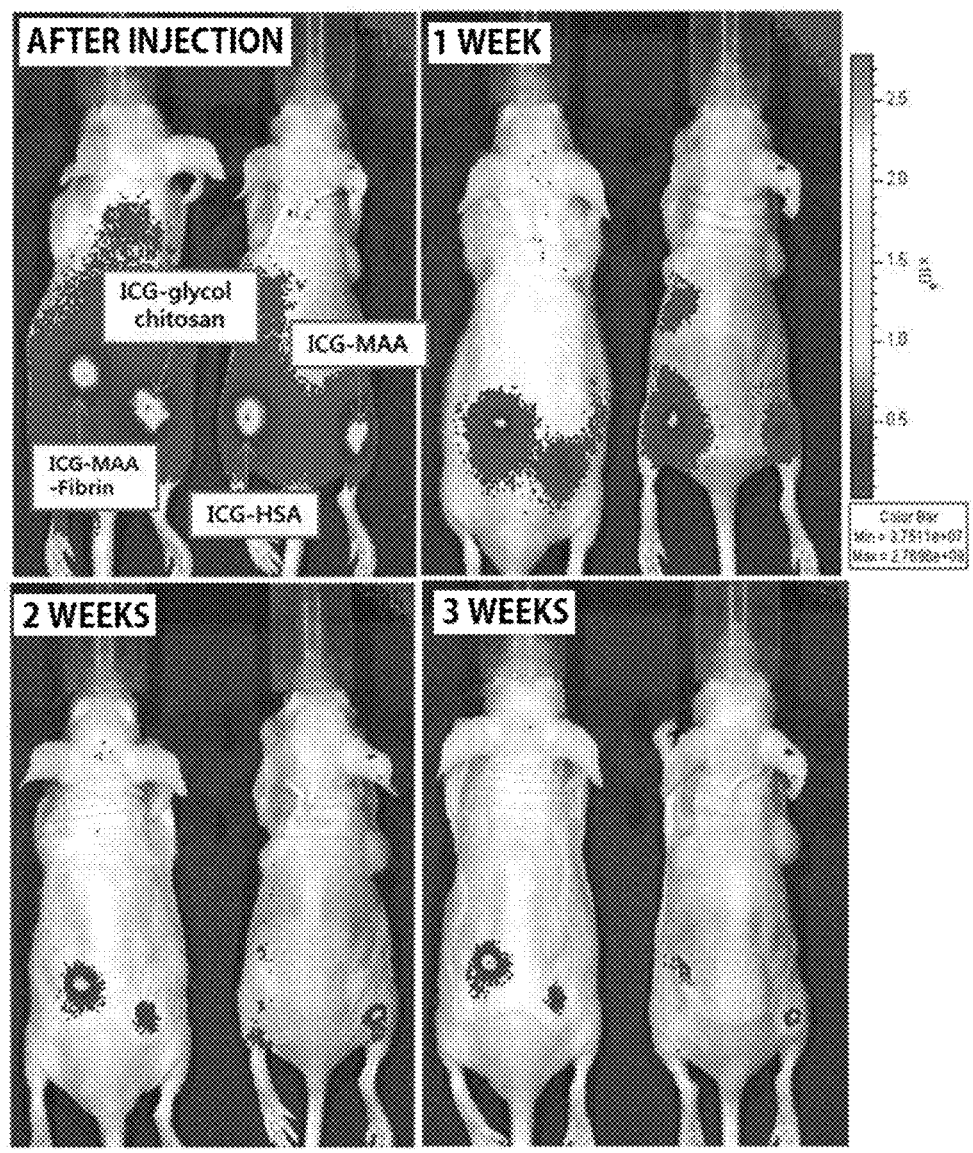

[Figure 7]
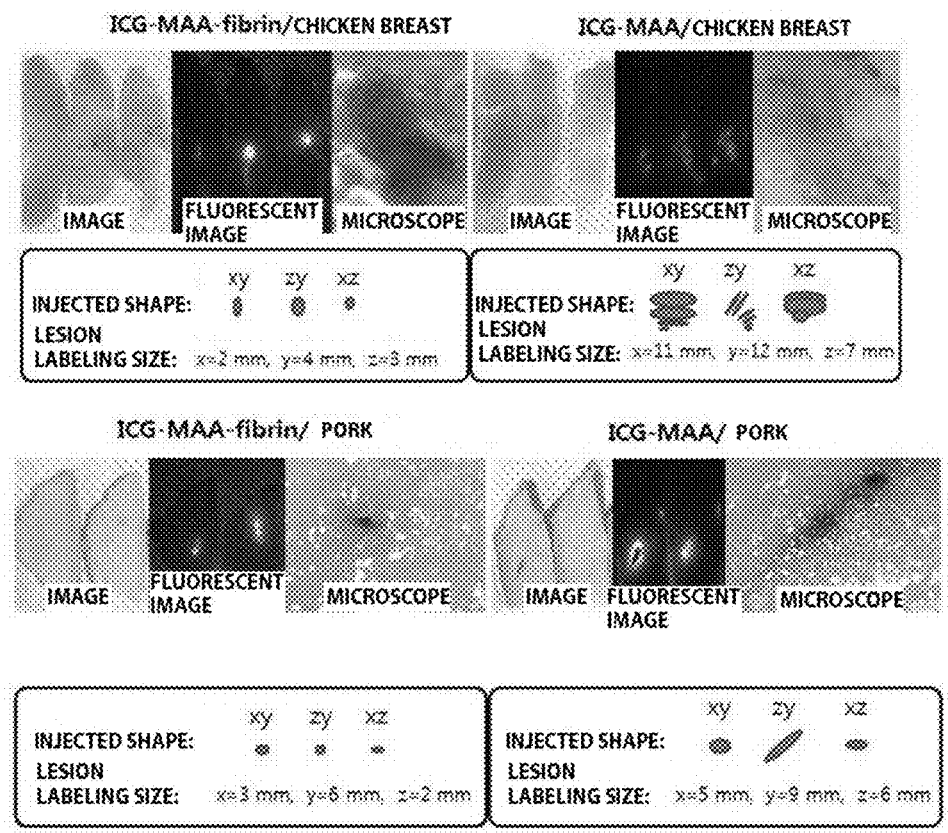

[Figure 8]
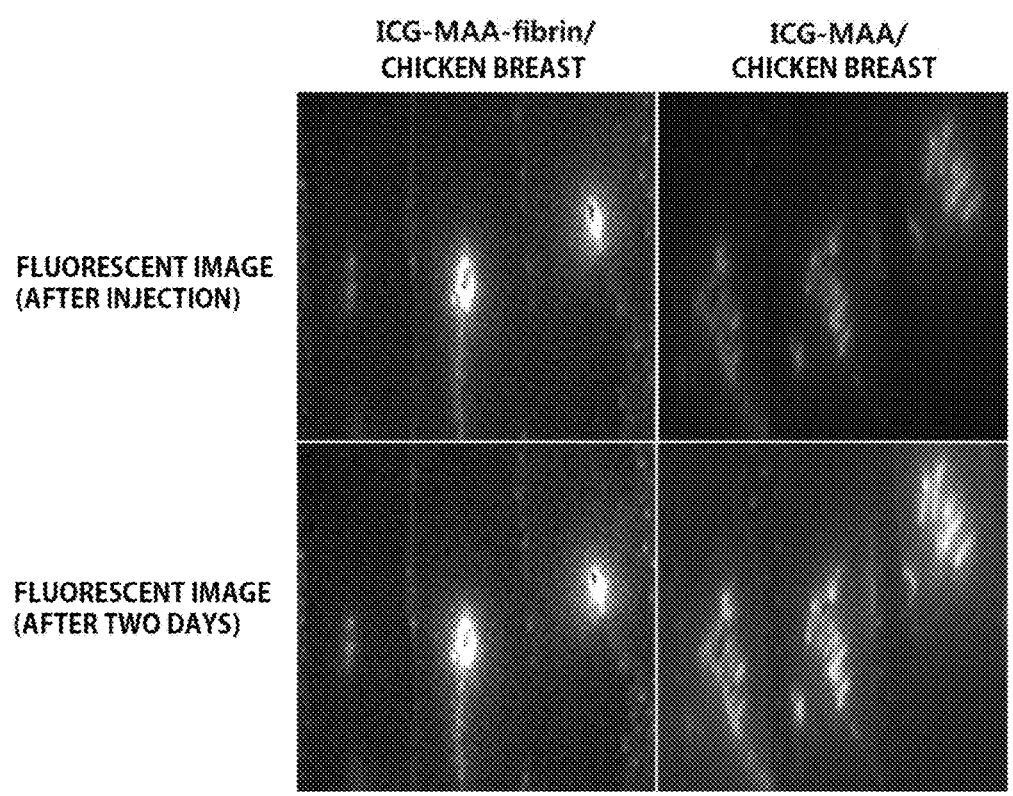

[Figure 9]
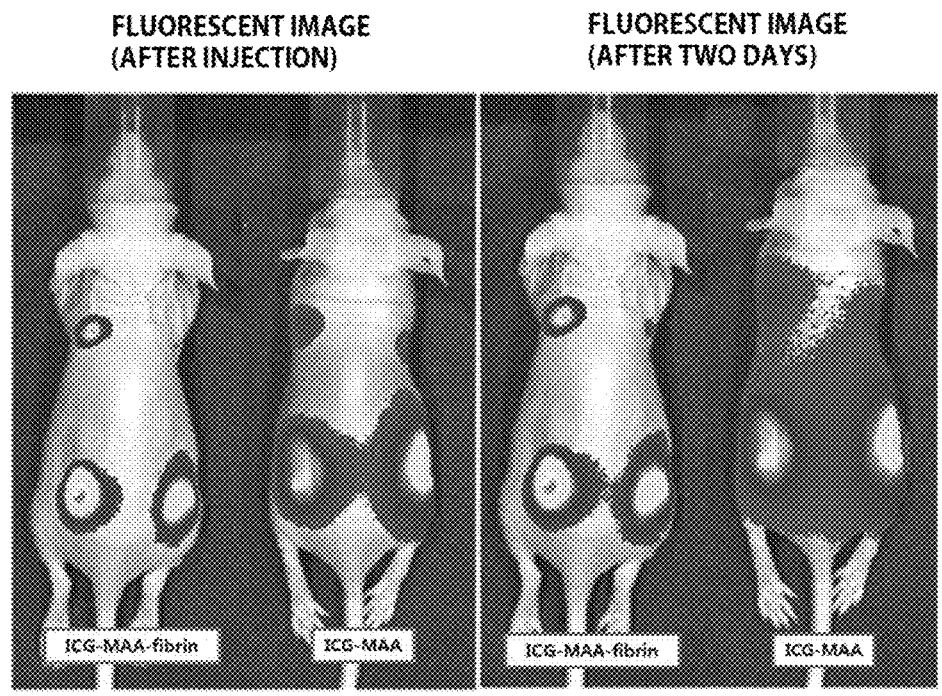
[Figure 10]
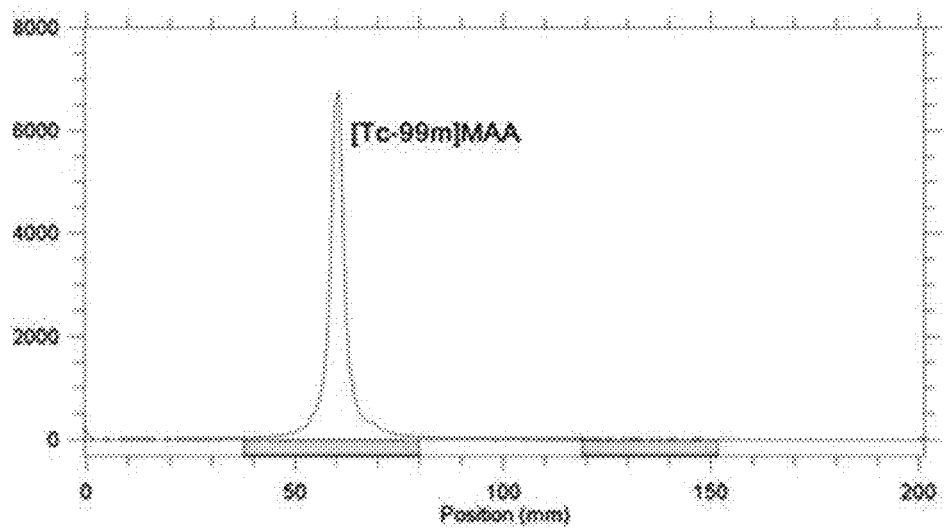

[Figure 11]
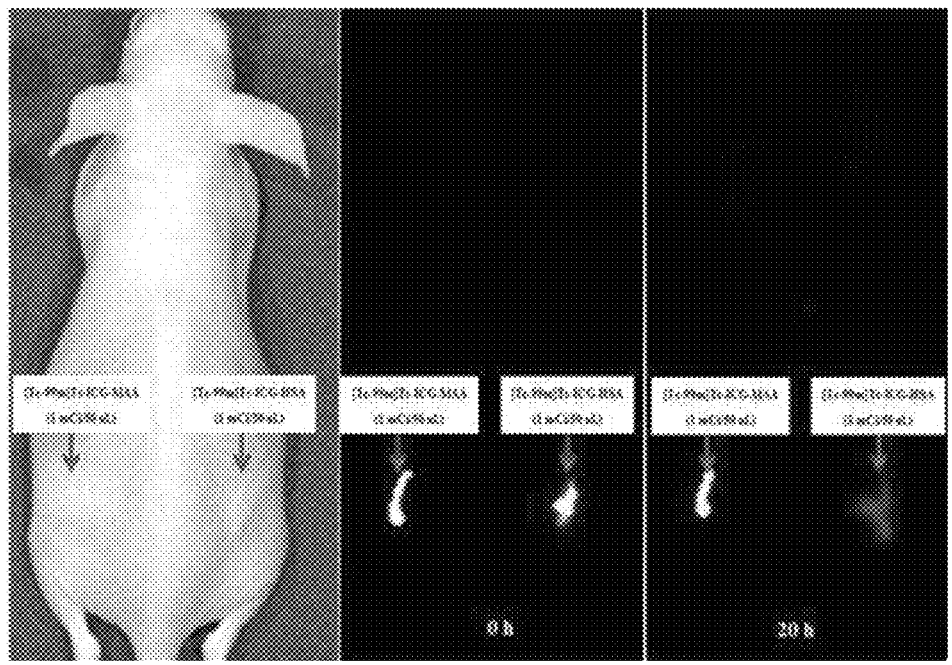
[Figure 12]
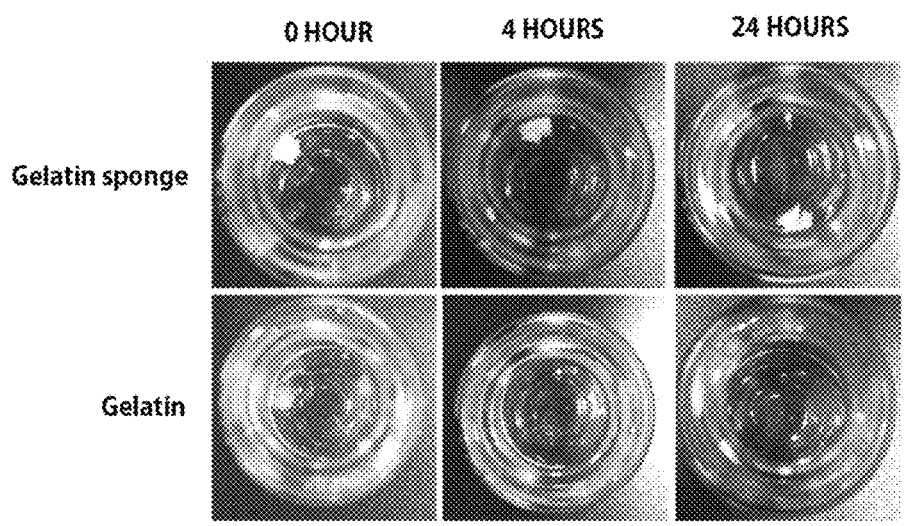

[Figure 13]
(Radiogoldcoil/ICG-MAA-Gelatin sponge): RADIO GOLD LEAF COIL-INDOCYANINE GREEN-BOUND MACROAGGREGATED-GELATIN SPONGE (RADIOGOLDCOIL/ICG-MAA-GELATIN SPONGE)
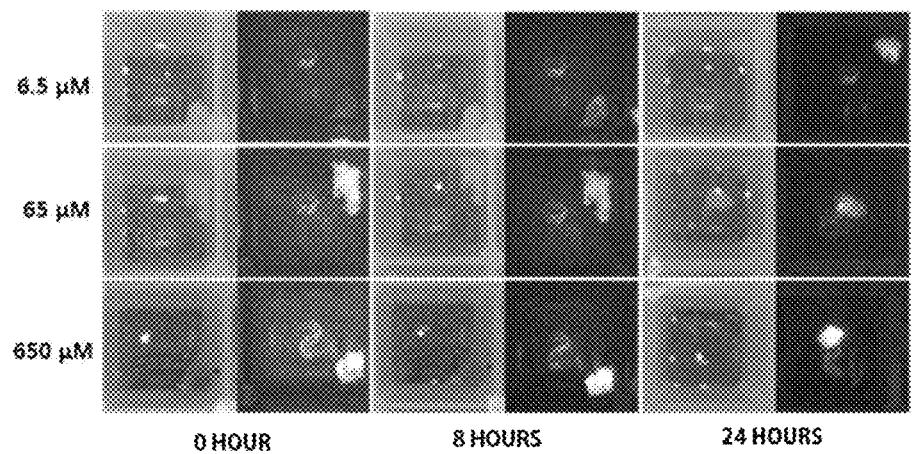
INDOCYANINE-BOUND SPONGOSTAN (ICG SPONGOSTAN)
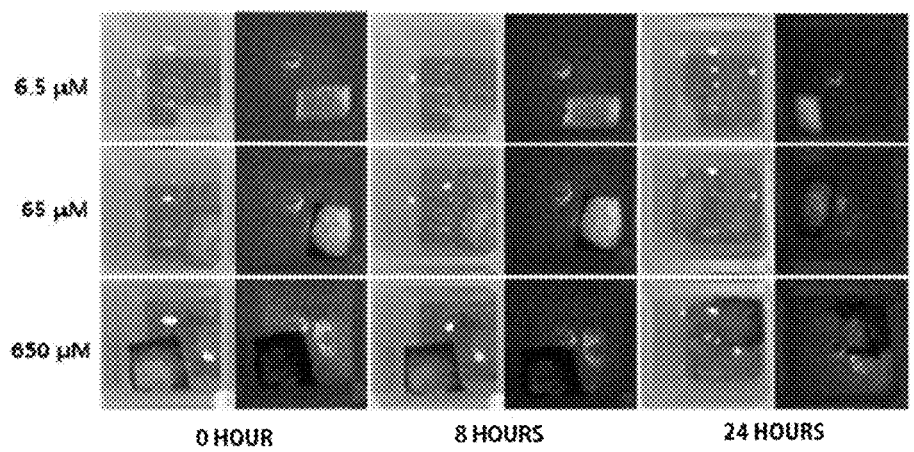

[Figure 14]
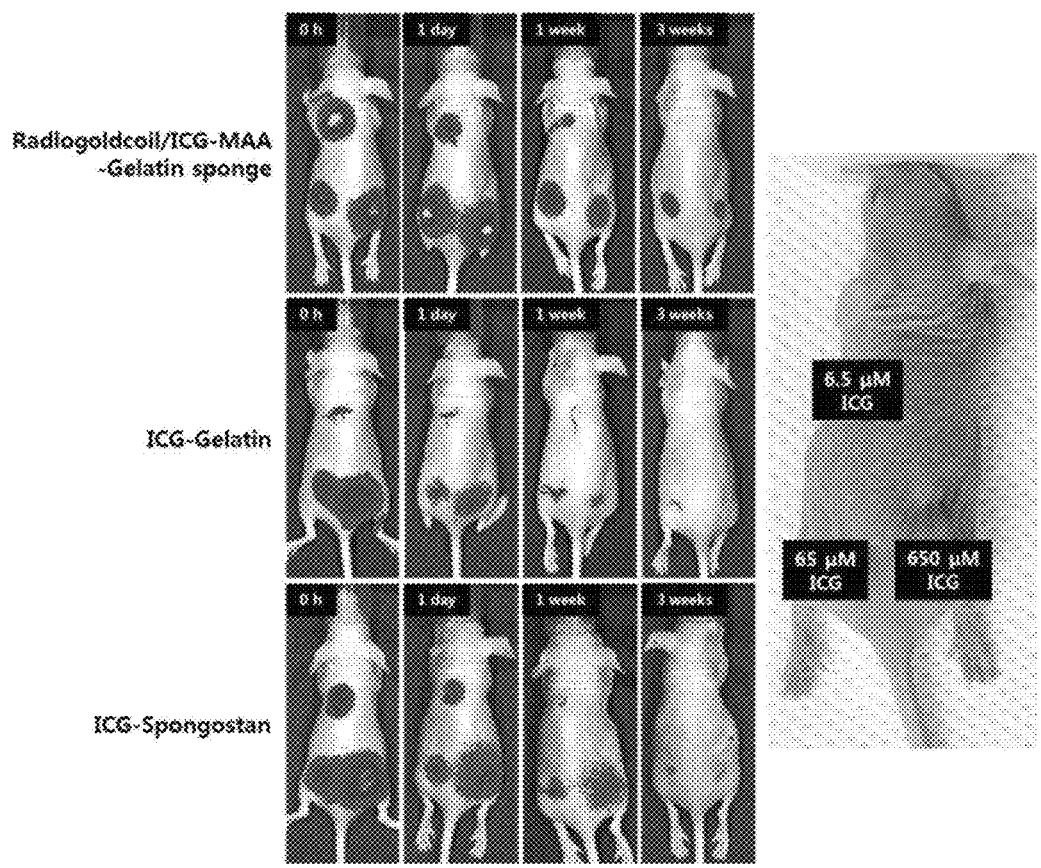

LABELING COMPOSITION FOR CANCER LESION

RELATED APPLICATIONS

This application is the U.S. National Phase of and claims priority to International Patent Application No. PCT/KR2013/011177, International Filing Date Dec. 4, 2013, entitled Novel Labeling Composition for Cancer Lesion, which claims benefit of Korean Patent Application No. 10-2012-0153793 filed Dec. 26, 2012; both of which are incorporated herein by reference in their entireties.

TECHNICAL FIELD

The present invention relates to a novel labeling composition for a cancer lesion. More particularly, the present invention relates to a labeling composition, for a cancer lesion, including a complex in which macroaggregated albumin (MAA) is bound to a pigment for staining living tissues, radioactive isotope, or combination thereof; a method for providing information about a cancer lesion site by using the labeling composition for a cancer lesion; a kit including the labeling composition for a cancer lesion for labeling a cancer lesion; and a complex in which a pigment for staining living tissues binds to MAA included in the labeling composition for a cancer lesion.

BACKGROUND ART

For anticancer therapy, a method using various anticancer agents has been developed, however a surgical operation method of removing cancer cells is still most frequently used method. When the surgical operation method is used, technique to minimize surgical extent during surgery is necessary for post-surgical health and wellbeing of patients. In particular, for breast cancer, a lesion excised during surgery should be smaller for Korean women than other countries whose breast size is small, in order to achieve a goal of breast preservation therapy. Surgical extent is determined as a lesion and boundary margin regions around the lesion. In the case where an operating surgeon does not precisely know extent and region of a lesion, a great size of boundary margin regions around the lesion should be required. The reason is that, when extension of surgery is blindly reduced, a tumor may remain in the incised side. However, in actual clinical surgery, there is little method to allow an operating surgeon to precisely identify the lesion in real time during surgery. Although a very precise diagnostic method has been developed, the diagnostic method may not be used during surgery. Thus, during actual surgery, tactile sensation and vision of an operating surgeon are mainly used. However, in such a case, it is rare to clearly distinguish the lesion. In particular, in the case where a lesion is small, it is more difficult to distinguish. In order to achieve a goal of microinvasive surgery and preservation surgery, a technique is necessary to inform an operating surgeon about a lesion in real time during surgery.

In a typical surgery to remove a tumor, in particular, breast cancer surgery, a microlesion site of a patient is identified before surgery by ultrasonic waves, mammography, or magnetic resonance imaging. Then, the identified site of a lesion is marked, and thereafter, tissue in the marked region is removed. As a method for marking the identified site of a lesion, following methods are used: a method of drawing a picture on a skin surface, a method of using a wire, and a method of injecting a black pigment such as charcoal. Although the method of drawing a picture on skin by using a pen to mark a site of a lesion can be easily used, the method has a drawback of low accuracy, because, due to a very flexible characteristic of breast tissue, a shape of breast is greatly changed during surgery from a shape at the point of diagnosis, and, in the case of a lesion at deep breast, a mark on a skin surface is insufficient. Also, a drawback of the method of inserting a wire into a breast lesion is lower accuracy than expected because essentially a wire should be vertically inserted into a skin surface, but the vertical insertion of the wire may affect an ultrasonic probe, so that the wire is inevitably inserted obliquely; and because a location of the wire may be moved according to movement of breast. In addition, another drawback of the method is that the inserted wire interferes with surgery; and a procedure to excise a site for inserting the wire should be additionally performed. Finally, the method of injecting a pigment such as charcoal is advantageous in that the injected pigment binds to a lesion so that a site of the lesion may be accurately labeled. However, in the case of a lesion in deep breast, there are drawbacks in that a black pigment may not be identified at the exterior, and a surgical region may be contaminated by the pigment. These drawbacks also become a limitation in a surgical operation to remove cancer tissue beside breast cancer.

Thus, through technique developed so far, it is difficult to precisely determine an extent of surgery for surgically removing a cancer lesion. Consequently, when a cancer lesion is surgically removed, an excised region needs to be larger than necessary, and also inspection of identifying whether the lesion is normally removed or not should be accompanied after surgery.

Therefore, the present inventors have completed the present invention by demonstrating that, when a cancer lesion is surgically removed, a labeling agent including macroaggregated albumin, to which a pigment for staining living tissues is bound, effectively adsorbs to the cancer lesion, so that a site of the lesion can be accurately labeled; and that the pigment can be traced in real time, so that a range of the lesion to be removed can be accurately identified.

DISCLOSURE OF THE INVENTION

Technical Problem

An object of the present invention is to provide a labeling composition for a cancer lesion, including a complex in which macroaggregated albumin (MAA) is bound to a pigment for staining living tissues, radioactive isotope, or combination thereof.

Another object of the present invention is to provide a method for providing information about a site of a cancer lesion by using the labeling composition for a cancer lesion.

Still another object of the present invention is to provide a kit for labeling a cancer lesion, the kit including the labeling composition for a cancer lesion.

Even another object of the present invention is to provide a complex in which a pigment for staining living tissues binds to MAA included in the labeling composition for a cancer lesion.

Technical Solution

To achieve the object, the present invention provides a labeling composition for a cancer lesion, including a complex in which macroaggregated albumin (MAA) is bound to a pigment for staining living tissues, radioactive isotope, or combination thereof. A cancer to be labeled with the composition may be any cancer including tissue where the MAA may penetrate and be immobilized thereon without limitation. However, the cancer is preferably a solid cancer having tissue where the MAA may penetrate and be immobilized thereon. Examples may include prostate cancer, breast cancer, uterus cancer, skin cancer, cervical cancer, lung cancer, brain tumor, gastrointestinal tumor, liver cancer, soft tissue sarcoma, and lymphoma, etc.

The wording "macroaggregated albumin (MAA)" used herein means proteinous particles which have a diameter of 10 to 50 µm and are prepared by heating and coagulating human serum albumin. A structure and physical property of MAA differs from human serum albumin having a diameter less than 10 nm. When the MAA is intravenously injected, the MAA may remain in pulmonary capillary, which is 8 µm, thereby causing microembolus. By using such a property, the MAA labeled with a radioactive isotope has been used for lung scintigram (for diagnosis of disorders in pulmonary blood flow, right-to-left shunt or lung increased venous pressure such as pulmonary embolism, pulmonary blood clot, pulseless disease, pneumonia, and lung cancer), venous scan (for in situ diagnosis of venous blood of central nerves) or venous scan (for diagnosis of peripheral artery blood flow disorders such as faza disease). The MAA of the present invention is injected into a cancer lesion tissue, and used as a mediator for binding a labeling material to the cancer lesion tissue. The MAA of the present invention may be synthesized by using recombinant HSA or non-autologous HSA. Also, commercially available MAA may be purchased and used. The MAA of the present invention is injected into a cancer lesion tissue and used as a mediator for binding a labeling material to the cancer lesion tissue, wherein the mediator adsorbs the labeling material to prevent the labeling material from diffusion to the cancer lesion tissue.

The wording "pigment for staining living tissues" used herein means a material which binds to living tissues thereby labeling the binding site in order to allow the labeled site to be identified with the naked-eye or by using a detection tool. For the purpose of the present invention, as the pigment for staining living tissues, a labeling material which can bind to cancer tissue and be used to label a site where cancer is generated. Preferably, a visible pigment, or fluorescent pigment, which generates fluorescence at the binding site and is detectable by using a device such as a fluorescence camera, may be used alone or in combination, but not limited thereto.

The wording "visible pigment" used herein means a type of pigment in which a labeling material binding to living tissues exhibits color of visible light wavelength, such that the labeled region can be identified with the naked-eye. For the purpose of the present invention, the visible pigment may be injected to a site where a cancer is generated, such that, when the cancer is surgically removed, a cancer lesion to be excised can be precisely identified, and thus a success rate of cancer surgery can be increased. Preferably, as the visible labeling material, natural red, nile blue, bismark brown, lithium carmine, trypan blue, janus green, methyl violet, o-lamine, malachite green, safranine, eosin, congo red, erythrocin, nigrosin, alcian blue hematoxylin, aniline blue, and light green may be used alone or in combination, but not limited thereto as long as the purpose of making it possible to identify cancer lesion tissue can be achieved.

The wording "fluorescent pigment" used herein means an organic compound which emits fluorescence to allow the penetration length of light to become maximum and to allow an error signal due to moisture to become minimum after an excitation state is formed by absorbing light having a certain wavelength. The fluorescent pigment may be a near-infrared fluorescent pigment which is an organic compound which preferably emits fluorescence at near-infrared wavelength of 700 nm to 3000 nm, and preferably 750 nm to 900 nm. Fluorescent at near-infrared wavelength generated from the near-infrared fluorescent pigment may be captured in an image form or monitored in real time by using a device such as a fluorescent camera, and fluorescence-sensing probe (PCT/KR2011/009271). In vivo absorption of fluorescence at near-infrared wavelength of the present invention is relatively lower than that of fluorescence at other wavelengths, such that near-infrared generated in a relatively deep portion of a body can be detected ex vivo. For the purpose of the present invention, the fluorescent pigment at near-infrared wavelength may be injected to a site where a cancer is generated to make the cancer lesion site to be accurately identified before excision when the cancer is surgically removed, and thus a success rate of cancer surgery may be increased. In particular, unlike the visible pigment, a site of a lesion may be detected ex vivo before directly identifying the lesion through excision, so that rapid and accurate cancer surgery may be achieved. As the near-infrared fluorescent pigment, indocyanine green is preferably used. However, as long as applicable to the human body, any near-infrared fluorescent pigment may be included in the scope of the present invention.

A complex, in which the near-infrared fluorescent pigment binds to MAA, is advantageous in that safety and accuracy of the detected fluorescent signal are better than those of a complex in which the near-infrared fluorescent pigment binds to other materials which are known to be accumulated in a tumor. Thus, a rate of capability to detect a microlesion is high, and excision accuracy of a lesion can be enhanced.

The wording "indocyanine green (ICG)" used herein means a fluorescent imaging dye of a near-infrared region which is widely used in biological and medical fields. Since the ICG is degraded and then removed or excreted into urine and feces about one hour after being injected into a human body, the ICG is advantageous in clinical application as a fluorescent dye applicable to the human body. Indeed, cases of applying ICG to the human body have been reported in many journals. As an example, it has been reported that, in clinical, ICG is safely used for 18 breast cancer patients (see T. Kitai, et al., Breast Cancer, 12:211-215, 2005). Also, adsorption and binding of the near-infrared fluorescent pigment may be achieved by mixing the near-infrared fluorescent pigment to MAA of the present invention.

According to an example of the present invention, during preparation of a complex in which MAA is bound to ICG (ICG-MAA), it has been found that an appropriate mixing ratio to prepare a complex showing a high level of a near-infrared fluorescent signal is 3.9 uM ICG to 0.23 mg/d of MAA, 6.5 µM ICG to 2.3 mg/d MAA, and 6.5 µM ICG to 11.5 mg/d MAA (Table 1 and FIG. 4). When being injected into a body, since concentrations are varied due to in vivo diffusion, exact concentration may not be determined at the point of injection. However, it has been experimentally found that the highest fluorescent value is shown at 65 µM which is 10 times higher concentration. In addition, as a result of investigating whether the constructed complex shows stability under both in vitro and in vivo conditions, it can be found that a relatively high level of fluorescent signal intensity and stability are shown under both in vivo and in vitro conditions (FIGS. 5 and 6).

The wording "radioactive isotope" used herein means an element which has the same atomic number but different atomic weight, thereby capable of emitting radioactivity, wherein the radioactive isotope is also generally used as an important labeling agent for diagnosing diseases by using a property of emitting gamma ray and other subatomic particles for radioactive decay. For the purpose of the present invention, the radioactive isotope may be injected into a cancer-generating site in deep tissue where fluorescence generated from the near-infrared fluorescent pigment is not detected, in order to make a cancer lesion to be accurately identified before excision, when the cancer is surgically removed, and thus a success rate of cancer surgery may be increased. The radioactive isotope may be any radioactive isotope which has a capability to label MAA capable of binding to a cancer lesion, but not specifically limited thereto. Preferably, the radioactive isotope may be H-3, C-14, P-32, S-35, Cl-36, Cr-51, Co-57, Co-58, Cu-64, Fe-59, Y-90, I-124, I-125, Re-186, I-131, Tc-99m, Mo-99, P-32, CR-51, Ca-45, and Ca-68, etc. More preferably, the radioactive isotope may be medically used I-124, I-125, I-131, Cu-64, Tc-99m, Mo-99, CR-51, Ca-45, and Ca-68, etc. Most preferably, Tc-99m may be used. The cancer may be any cancer which may be removed through surgical resection without limitation. The cancer may be most solid cancers such as prostate cancer, breast cancer, uterus cancer, skin cancer, cervical cancer, lung cancer, brain tumor, gastrointestinal tumor, liver cancer, soft tissue sarcoma, and lymphoma, but not limited thereto.

The wording "Tc-99m" used herein is a radioactive isotope of technetium (Tc) which has a short half life of 6 hours, emits gamma ray thereby being used for imaging, shows a very little exposure dose and excellent tissue-penetrating rate, and does not cause an allergic response which is shown in some pigments. Thus, Tc-99 m is widely used in a medical research.

According to an example of the present invention, when MAA is reacted to [Tc-99m]TcO$_4^-$, which is a radioactive isotope, a complex in which the radioactive isotope binds to MAA at an yield of 99% or more can be constructed. When the complex is injected into a body, an injected site can be identified until 20 hours after injection (FIG. 3). When the MAA is sequentially reacted with [Tc-99m]TcO$_4^-$, which is a radioactive isotope, and ICG, which is a near-infrared pigment, a complex, to which the radioactive isotope and near-infrared fluorescent pigment are bound ([Tc-99m]Tc-ICG-MAA), can be constructed (FIG. 10). An injected site of the constructed complex can be identified after 20 hours of injection into a body (FIG. 11).

To maximize applicability of the complex in which a pigment for staining a living tissue binds to MAA of the present invention as an in vivo labeling agent, a physical property of the complex may be improved by using fibrin. Namely, the complex of the present invention is injected into a lesion region in a body in order to play a role of labeling the lesion to allow the lesion region to be clearly recognized during surgery. For the complex to easily achieve the goal as a labeling agent described above, diffusion should be maximally prevented at the lesion site injected. As a tool to achieve the goal, fibrin may be used (FIG. 1). FIG. 1 is a schematic diagram showing that, when fibrin is added to a complex including MAA and ICG, in vivo retention of the complex in tissue is enhanced by the added fibrin. As shown in FIG. 1, the fibrin plays a role in binding of the complexes injected into a body together, and thus the complexes injected into a body can be maximally prevented from being diffused. Thus, the complex of the present invention may further include fibrin.

According to an example of the present invention, an ICG-MAA-fibrin complex, to which blood coagulation fibrin is bound, is constructed by mixing and reacting the mixture 1 and mixture 2 with the constructed complex (ICG-MAA) in which MAA is bound to ICG, wherein the mixture 1 includes thrombin and aprotinin, and the mixture 2 includes fibrinogen and CaCl$_2$. It has been investigated whether the ICG-MAA fibrin complex thus constructed shows stability under both in vitro and in vivo conditions, and, as a result, it has been found that a relatively high level of near-infrared fluorescent signal intensity and stability are shown in both in vitro and in vivo conditions (FIGS. 5 and 6). Also, since a diffusion degree with the lapse of time of the ICG-MAA-fibrin complex is lower than that of the complex in which MAA is bound to ICG (ICG-MAA) under in vitro and in vivo conditions, it has been found that the ICG-MAA-fibrin complex shows an advantageous property as a labeling agent for a cancer lesion (FIGS. 7, 8, and 9).

Moreover, as described above, as another tool to achieve a purpose of preventing in vivo diffusion of the complex, gelatin sponge may be used. When gelatin which has an excellent in vivo compatibility and can easily form gel at room temperature is used, a construct, in which the complex is encaptured in an aggregated form within the gelatin, may be formed. By injecting the construct thus formed into a body, diffusion of the complex at the injection site may be maximally inhibited by gelatin. However, the gelatin has a limitation, in which the gelatin is easily dissolved in vivo environment, and thus the construct may be destroyed. To overcome the limitation, gelatin sponge is used instead of gelatin, so that the limitation can overcome.

Gelatin sponge is a construct in which an isopeptide bond is produced between an amine group of a side chain of lysine and a carboxylic group of a side chain of glutamate or aspartate present in gelatin by heating a gelatin solution at high temperature. The gelatin sponge shows in vivo compatibility the same as that of gelatin, while having relatively low solubility to water, and thus the gelatin sponge is not easily dissolved in a body. Thus, when forming a construct in which the complex of the present invention is encaptured in an aggregated form by using the gelatin sponge and injecting the construct to the body, since the gelatin sponge is not dissolved in a body, the injected construct is not destroyed. Thus, diffusion of the complex at the injected site may be more effectively inhibited.

According to an example of the present invention, gelatin sponge including a cross structure is prepared by heating the gelatin solution for 3 hours at 160° C., and each of gelatin and gelatin sponge is immersed in distilled water and left for 24 hours. As a result, it has been found that gelatin is completely dissolved in distilled water, while gelatin sponge is not dissolved in water, indicating higher stability (FIG. 12).

When the gelatin sponge described above is used, a construct may be prepared to include a near-infrared fluorescent pigment and radioactive isotope together. Namely, a construct may be constructed to include a complex in which MAA is bound to a near-infrared fluorescent pigment ICG (ICG-MAA), or a complex in which MAA is bound to a radioactive isotope [Tc-99m]Tc and a near-infrared fluorescent pigment ICG ([Tc-99m]Tc-ICGMAA) in the gelatin sponge. In addition, a construct may be constructed to separately include a radioactive isotope and a complex in which MAA is bound to a near-infrared fluorescent pigment ICG (ICG-MAA) in the gelatin sponge. As such, in the case where the complex and the radioactive isotope are separately included, a tool may be further included to effectively immobilize the radioactive isotope in the gelatin sponge. As the immobilizing tool, a radioactive isotope-bound gold leaf coil may be used, but not specifically limited thereto, as long as the immobilizing tool achieves the purpose of immobilizing the radioactive isotope (FIG. 2). FIG. 2 is a schematic diagram showing a structure and injection method of a solid-type labeling agent constructed by adding a radioactive isotope-bound gold leaf coil, and gelatin to the complex including MAA and ICG. As shown in FIG. 2, the labeling agent may be constructed by using a complex to which a radioactive isotope is not bound (ICG-MAA) and adding the radioactive isotope as necessary. Therefore, by using the gelatin sponge, applicability of the MAA-based labeling agent may be enhanced.

According to an example of the present invention, a solid-type labeling agent including a radioactive isotope-bound gold leaf coil, ICG, MAA and gelatin sponge is constructed, and stability thereof is compared under in vitro and in vivo conditions with that of a control solid-type labeling agent which only includes ICG and gelatin sponge. As a result, it has been found that, under in vitro condition, ICG in the control solid-type labeling agent is diffused and thus a near-infrared fluorescent signal is detected in distilled water per se after 8 and 24 hours, while an ICG diffusion rate of the solid-type labeling agent of the present invention is in a relatively low level (FIG. 13). Also, it has been found that, under in vivo condition, no more near-infrared fluorescent signal is detected for the control solid-type labeling agent after three weeks, while a near-infrared fluorescent signal is still detected for the solid-type labeling agent of the present invention (FIG. 14).

According to another aspect of the present invention, the present invention provides a method for providing information about a site of a cancer lesion including: (a) administering the labeling composition for a cancer lesion to a cancer lesion generated in a subject; and (b) identifying a site generating a signal selected from the group consisting of color, near-infrared fluorescence, radioactivity and combination thereof from the subject.

The wording "subject" used herein means a living organism in which a cancer may be generated to thereby exhibit a lesion, and to which the labeling complex or composition for a cancer lesion of the present invention may be administered.

When the labeling composition for a cancer lesion provided in the present invention is administered to cancer lesion tissue of a body, the administered composition binds to the cancer lesion, and thus a site of the lesion can be labeled through color, near-infrared fluorescence, radioactivity or combination thereof. By detecting the label, it is possible to detect a site and size of the cancer lesion in real time during surgery. Therefore, accuracy can be enhanced and excessive loss of normal tissue can be prevented during surgical removal of a cancer lesion.

In addition, the complex included in the composition of the present invention may remain in a cancer lesion in a body for a long period of time relative to a complex in which a pigment for staining a living tissue binds to other materials, and thus accuracy of cancer lesion excision can be easily verified during a surgical procedure, as well as surgical excision of the cancer lesion. For example, through ultrasound, a microlesion site is identified before surgery. Then the complex of the present invention is injected into the lesion region to make the lesion region to be stably and accurately identified during surgery which is performed few hours after.

As still another aspect of the present invention, the present invention provides a kit including the composition for labeling a cancer lesion and a complex in which a pigment for staining living tissue binds to MAA included in the composition. The kit or complex may be used to identify a site and size of cancer lesion tissue in real time during cancer-removing surgery.

BRIEF DESCRIPTION OF THE DRAWINGS

FIG. 1 is a schematic diagram showing that, when fibrin is added to a complex including MAA and ICG, in vivo retention of the complex in tissue is enhanced by the added fibrin.

FIG. 2 is a schematic diagram showing a structure and injection method of a solid-type labeling agent constructed by adding a radioactive isotope-bound gold leaf coil, and gelatin to the complex including MAA and ICG.

FIG. 3 is a gamma image showing whether [Tc-99m]Tc-MAA is changed or not with the lapse of time in a nude mouse injected with [Tc-99m]Tc-MAA.

FIG. 4 is a graph showing changes in signal intensity of near-infrared fluorescence of ICG-MAA complexes depending on concentration changes of ICG and MAA.

FIG. 5 is a graph showing changes in intensity of near-infrared fluorescent signals of ICG-HSA, ICG-MAA, ICG-MAA-fibrin and ICG-glycol chitosan complexes with the lapse of time under in vitro condition.

FIG. 6 is a graph showing changes with the lapse of time in intensity of near-infrared fluorescent signals of ICG-HSA, ICG-MAA, ICG-MAA-fibrin and ICG-glycol chitosan complexes, which are injected into nude mice.

FIG. 7 is images showing a shape of each complex observed in pork belly or chicken breast injected with the ICG-MAA-fibrin complex or ICG-MAA complex.

FIG. 8 is a fluorescent image showing diffusion levels of the ICG-MAA-fibrin complex and ICG-MAA complex injected into muscle tissue with the lapse of time.

FIG. 9 is a fluorescent image showing diffusion levels of the ICG-MAA-fibrin complex and ICG-MAA complex injected into nude mice with the lapse of time.

FIG. 10 is a graph showing a labeling rate of a complex in which MAA is bound to Tc-99m.

FIG. 11 is an image showing changes in a fluorescent signal of each labeling agent in mice with the lapse of time, wherein the mice are respectively administered with [Tc-99m]Tc-ICG-MAA and [Tc-99m]Tc-ICG-HAS, which are labeling agent for a cancer lesion.

FIG. 12 is an image showing a result of comparing diffusion levels of gelatin and gelatin sponge with the lapse of time.

FIG. 13 is an image showing changes in intensity of near-infrared fluorescent signals of a solid-type labeling agent and a control ICG-spongostan with the lapse of time, wherein the solid-type labeling agent includes a radioactive isotope-bound gold leaf coil, ICG, MAA and gelatin sponge.

FIG. 14 is an image showing intensity of near-infrared fluorescent signals of the solid-type labeling agent, ICG-Spongostan and ICG gelatin, which are injected into nude mice, with the lapse of time.

MODE FOR CARRYING OUT THE INVENTION

Hereinafter, the present invention will be described in more detail with reference to the following examples. However, these examples are only to illustratively describe the present invention, and the scope of the invention is not limited thereto.

Example 1: Construction of Macroaggregated Albumin (MAA)

10 ml and of 2% human serum albumin diluted in 0.1 M acetate buffer (pH 5.4) was mixed with 50 mg of tin chloride, and vigorously stirred for 10 minutes at room temperature followed by additional stir for 20 minutes at 70° C. for reaction. After the reaction was stopped, the reactant was cooled. Then, 0.35 ml and of 20% human serum albumin was added, and the resultant was stirred again for 10 minutes. The reactant was aliquot to a glass vial (2 mg for each, based on MAA) and lyophilized to prepare thiol MAA.

Example 2: Radioactive Isotope-Bound MAA Complex and Investigation of Availability Thereof 2 ml and of [Tc-99m]TcO$_4^-$ (10 mCi/ml), which is a radioactive isotope, was added to the thiol MAA constructed in Example 1. The resultant mixture was reacted for 10 minutes at room temperature to construct a radioactive isotope-bound MAA complex ([Tc-99m]Tc-MAA). To investigate whether the radioactive isotope normally binds to MAA, the complex is applied on instant thin layer chromatography (ITLC), and developed by using acetone as a solvent, and, as a result, it has been found that at least 99% of thiol MAA binds to the radioactive isotope, thereby forming a complex.

In addition, to investigate whether the constructed complex may be used as an in vivo labeling agent, an experiment was performed as follows: the constructed [Tc-99m]Tc-MAA 1 mCi/50 μl was injected into a left buttock of a nude mouse. A gamma image of the nude mouse was taken by using an animal SPECT device (NanoSPECT, Bioscan) at immediately after injection (0 h) and 20 hours after injection (20 h) (FIG. 3). FIG. 3 is a gamma image showing whether [Tc-99m]Tc-MAA is changed or not with the lapse of time in the nude mouse injected with [Tc-99m]Tc-MAA. As shown in FIG. 3, it has been found that, at immediately after (0 h) and 20 hours after (20 h) injection, [Tc-99m]Tc-MAA was continued to persistently remain in the injected lesion.

Example 3: Preparation of Indocyanine Green (ICG)-Bound MAA-Based Labeling Agent and Investigation of Availability Thereof Since it has been expected that a complex, in which MAA binds to indocyanine green (ICG) capable of generating a near-infrared fluorescent signal, may be used as a labeling agent stably acting in vivo, the complex was constructed and availability thereof as an in vivo labeling agent was investigated.

Example 3-1: Determination of Mixing Ratio of ICG and MAA

To prepare a MAA-based labeling agent exhibiting near-infrared fluorescence, indocyanine green exhibiting near-infrared fluorescence was bound to the constructed MAA to construct a complex (ICG-MAA).

To determine a mixing ratio of MAA and ICG which makes it possible to exhibit the strongest near-infrared fluorescence, ICG of 1.3 to 1032 μM and MAA of 0 to 11.5 mg/and were reacted at various ratios to construct respective ICG-MAA complex. Then, signal intensity of near-infrared fluorescence generated by each of the constructed ICG-MAA complex was measured (Table 1 and FIG. 4). FIG. 4 is a graph showing changes in signal intensity of near-infrared fluorescence of the ICG-MAA complex depending on concentration changes of ICG and MAA.

TABLE 1

Signal intensity of near-infrared fluorescence of ICG-MAA complex depending on concentration change of ICG and MAA

| ICG(μM) | MAA(mg/ml) | | | |
|---|---|---|---|---|
| | 0 | 0.23 | 2.3 | 11.5 |
| 1.3 | 18 | 42 | 238 | 530 |
| 3.9 | 120 | 52 | 424 | 931 |
| 6.5 | 212 | 38 | 456 | 979 |
| 9.0 | 289 | 32 | 444 | 942 |
| 12.9 | 363 | 27 | 342 | 915 |
| 25.8 | 466 | 12 | 255 | 563 |
| 38.7 | 425 | 8 | 162 | 366 |
| 51.6 | 399 | 7 | 101 | 280 |
| 64.5 | 374 | 13 | 75 | 244 |
| 77.4 | 332 | 16 | 55 | 182 |
| 103 | 289 | 23 | 39 | 94 |
| 258 | 139 | 30 | 16 | 60 |
| 516 | 71 | 13 | 2 | 20 |
| 774 | 39 | 6 | 2 | 9 |
| 1032 | 30 | 6 | 1 | 4 |

As shown in Table 1 and FIG. 4, when MAA was not treated, 25.8 μM of ICG showed the highest value of signal intensity of near-infrared fluorescence. When 0.23 mg/d of MAA was treated, 3.9 μM of ICG showed the highest value of signal intensity of near-infrared fluorescence. When 2.3 mg/and of MAA was treated, 6.5 μM of ICG showed the highest value of signal intensity of near-infrared fluorescence. When 11.5 mg/d of MAA was treated, 6.5 μM of ICG also showed the highest value of signal intensity of near-infrared fluorescence.

For in vivo injection, concentration was changed due to in vivo diffusion, etc., so that exact concentration may not be determined at the point of injection. However, it has been experimentally found that 65 μM, which is 10 times concentration, showed the highest value of fluorescence.

Example 3-2: Construction of ICG-Bound Complex

By using the result obtained from the examples, various ICG-bound complexes were constructed.

Firstly, 65 μM of ICG was added and reacted to human serum albumin (HSA), glycol chitosan or MAA to construct the respective complexes (ICG-HSA, ICG-MAA and ICG-glycol chitosan).

The ICG-MAA thus constructed was mixed and reacted with the mixture 1 and mixture 2 to construct an ICG-MAA-fibrin complex to which blood coagulation fibrin was bound, wherein the mixture 1 includes throbine and aprotinin and the mixture 2 includes fibrinogen and CaCl$_2$. The mixing rates of the fibrinogen, aprotinin, throbine, and CaCl$_2$ were 25 mg/ml, 500 KIU/ml, 250 IU/ml and 4 mg/ml, respectively.

Example 3-3: Investigation of Stability of Near-Infrared Fluorescence of ICG-Bound Complex Due to the using characteristic, since a labeling composition for tissue having a longer period of time of emitting fluorescence is advantageous in use in an operation room when the composition is injected into a living tissue and labels the injected site, in vitro or in vivo stability of near-infrared fluorescence of 4 complexes constructed above was investigated.

Example 3-3-1: Investigation of In Vitro Stability

Intensity of near-infrared fluorescent signals emitted by four complexes constructed in Example 3-2 under in vitro condition was measured for 800 hours (FIG. 5). FIG. 5 is a graph showing changes in intensity of near-infrared fluorescent signals of ICG-HSA, ICG-MAA, ICG-MAA-fibrin and ICG-glycol chitosan complexes with the lapse of time under in vitro condition. As shown in FIG. 5, it has been found that complexes including ICG-MAA showed a relatively high level of intensity and stability of near-infrared fluorescent signals. Also, it can be found that ICG-MAA-fibrin showed a relatively high level of intensity and stability of a near-infrared fluorescent signal than ICG-MAA.

Example 3-3-2: Investigation of In Vivo Stability

50 μl of four complexes constructed in Example 3-2 were respectively injected into thigh of nude mice. Then, changes in near-infrared fluorescent signals generated in each nude mouse were measured by using Xenogen Lumina device for 3 weeks (FIG. 6). FIG. 6 is an image showing changes with the lapse of time in intensity of near-infrared fluorescent signals of ICG-HSA, ICG-MAA, ICG-MAA-fibrin and ICG-glycol chitosan complexes injected into the nude mice. As shown in FIG. 6, high levels of near-infrared fluorescent signals were exhibited in all four complexes at immediately after injection. However, after one week, near-infrared fluorescent signals exhibited in ICG-HSA and ICG-glycol chitosan complexes were rapidly reduced. After three weeks, almost no near-infrared fluorescent signal was detected in ICG-HSA and ICG-glycol chitosan complexes. In contrast, it has been found that near-infrared fluorescent signals exhibited in ICG-MAA and ICG-MAA-fibrin complexes were remained at a certain level after three weeks.

Through the result of the Examples, it can be found that complexes including ICG-MAA showed a relatively high level of in vitro and in vivo near-infrared signal intensity and stability. It has been expected that, although the same near-infrared fluorescent pigment was used, the different results were derived, because the complexes, which do not include ICG-MAA, would be degraded and absorbed into a body within a relatively short time. In particular, it can be found that ICG-MAA-fibrin showed a very advantageous property as a labeling agent for a cancer lesion by showing high stability of maintaining a shape due to added blood coagulation fibrin beside MAA.

Example 3-4: Comparison of Availability of ICG-MAA-Fibrin Complex and ICG-MAA Complex Since it has been found that the ICG-MAA-fibrin complex and ICG-MAA complex, which include ICG-MAA, showed a very advantageous property as a labeling agent for a cancer lesion through results of Example 3-3, effects of each complex as a labeling agent for a cancer lesion were compared.

Example 3-4-1: Comparison of Injected Forms in Tissue

Each complex was injected into chicken breast, which is a type of muscle tissue, or pork belly, which is a type of adipose tissue. Then, the injected tissue was dissected in a thickness of 1 to 2 mm. Thereafter, forms of each complex observed in each dissected tissue were compared (FIG. 7). FIG. 7 is images showing a form of each complex observed in pork belly or chicken breast injected with the ICG-MAA-fibrin complex or ICG-MAA complex. As shown in FIG. 7, it has been found that there arises a phenomenon, in which, when the ICG-MAA fibrin complex was injected, the complex was immediately coagulated in tissue and maintained an oval shape, however, when the ICGMAA complex was injected, the complex was diffused to muscle tissue along with a grain of muscle, and the complex was diffused in adipose tissue along with a needle mark.

Thus, it can be found that, when ICG-MAA-fibrin, which is coagulated with blood coagulation fibrin, was injected into living tissue, the complex was less diffused than ICG-MAA even in dense connective tissue, and thus it is possible to more delicately label a lesion.

Example 3-4-2: Comparison of Diffusion Level in Tissue with Lapse of Time

It has been expected that, when each complex injected into living tissue was diffused in the tissue, a region exhibiting a near-infrared fluorescent signal became widen, such that a role of delicately labeling a lesion region may be restricted.

To investigate that, the ICG-MAA-fibrin complex and ICG-MAA complex were injected into chicken breast, and diffusion levels of near-infrared fluorescent signals exhibited by each complex were compared at the point of injection and two days after injection (FIG. 8). FIG. 8 is a fluorescent image showing diffusion levels of the ICG-MAA-fibrin complex and ICG-MAA complex injected into muscle tissue with the lapse of time. As shown in FIG. 8, it can be found that coagulation occurred after injection of the ICG-MAA-fibrin complex, such that ICG-MAA was locked in fibrin, and thus, even after time has passed, increment in a size of a region exhibiting a near-infrared fluorescent signal caused by diffusion did not occur, however a region of exhibiting a near-infrared fluorescent signal for the ICG-MAA complex was increased with the lapse of time.

Example 3-4-3: Comparison of Diffusion Level in Mouse with Lapse of Time

To investigate whether the results from Examples may be applied in vivo, a nude mouse was subcutaneously injected with the ICG-MAA-fibrin complex or ICG-MAA complex. Then, diffusion levels of near-infrared fluorescent signals exhibited by each complex were measured by using Xenogen Lumina device at the point of injection and two days after injection (FIG. 9). FIG. 9 is an image showing diffusion levels of the ICG-MAA-fibrin complex and ICG-MAA complex injected into the nude mice with the lapse of time. As shown in FIG. 9, similar to the result of FIG. 8, it can be found that coagulation occurred after injection of the ICG-MAA-fibrin complex, such that ICG-MAA was locked in fibrin, and thus, even after time has passed, increment in a size of a region exhibiting a near-infrared fluorescent signal caused by diffusion did not occur, however a region of exhibiting a near-infrared fluorescent signal for the ICG-MAA complex was increased with the lapse of time.

Thus, it has been found that the ICG-MAA-fibrin complex showed a low level of diffusion over time, and as well as showed the most outstanding fluorescence and in vivo stability, thereby exhibiting an advantageous property as a labeling agent for a cancer lesion.

Example 4: Preparation OF [Tc-99m]Tc-ICG-MAA and Investigation of Effects

Example 4-1: Preparation OF [Tc-99m]Tc-ICG-MAA

To the MAA constructed in Example 1, was added [Tc-99m]TcO4– 20 mCi/2 ml. Then, the resultant mixture was reacted for 10 minutes at room temperature. After the reaction was stopped, 42 µg/µl of indocyanine green (ICG) was added, followed by additional reaction for 10 minutes at room temperature to prepare a complex in which MAA was labeled with a near-infrared fluorescent pigment, i.e. ICG and a radioactive isotope, i.e. Tc-99m.

To investigate whether the constructed complex was normally labeled with Tc-99m, the complex was applied on instant thin layer chromatography (ITLC) and developed by using acetone as a solvent (FIG. 10). FIG. 10 is a graph showing a labeling rate of the complex in which MAA was bound to Tc-99m. As shown in FIG. 10, it can be found that the labeling rate was at least 99%. In addition, a near-infrared fluorescent signal of ICG was measured by using Safire II fluorescent device (RFU 7,612).

Thus, it has been found that the [Tc-99m]Tc-ICG-MAA complex may be prepared by using MAA.

Example 4-2: Investigation of Effects of [Tc-99m]Tc ICG-MAA

In terms of a dilution level in living tissues with the lapse of time, the complex of the present invention was compared with a typical labeling agent for a cancer lesion to investigate whether the complex of the present invention may be applied as a labeling agent for a cancer lesion.

Specifically, a complex ([Tc-99m]Tc-ICG-HSA), in which human serum albumin was labeled with a near-infrared fluorescent pigment, i.e., ICG, and a radioactive isotope, i.e., Tc-99m, was prepared as a typical labeling agent for a cancer lesion.

1 mCi/50 µl of the constructed complex ([Tc-99m]Tc-ICG-HSA) was injected into a right buttock of a nude mouse, and 1 mCi/50 µl of the complex constructed in Example 4-1 ([Tc-99m]Tc-ICG-MAA) was injected into a left buttock of the nude mouse. Then, an gamma image of the nude mouse was taken by using an animal SPECT device (NanoSPECT, Bioscan) at immediately after injection (0 h) and 20 hours after injection (20 h) (FIG. 11). FIG. 11 is an image showing changes in fluorescent signals with the lapse of time for each labeling agent in the mice respectively administered with [Tc-99m]Tc-ICG-MAA and [Tc-99m]Tc-ICG-HSA which are labeling agent for a cancer lesion. As shown in FIG. 11, it has been found that, at immediately after injection (0 h), both complexes remained only in the injected lesion, however, at 20 hours after injection (20 h), [Tc-99m]Tc-ICG-HSA was diffused into adjacent tissues so that the fluorescent signal became weaker, while [Tc-99m]Tc-ICG-MAA was continued to persistently remain in the injected lesion.

Example 5: Preparation of MAA-Based Labeling Agent Using Gelatin and Investigation of Availability Thereof Since it has been expected that a labeling agent, which acts in vivo in a more stable manner, can be constructed by using gelatin sponge which shows high in vivo compatibility during preparation of a complex in which MAA binds to indocyanine green (ICG) capable of generating a near-infrared fluorescent signal; and simultaneously shows stability (which means the complex does not easily degraded in vivo), a complex using the gelatin sponge was constructed and availability thereof as an in vivo labeling agent was investigated.

Example 5-1: Preparation of Radioactive Isotope-Bound Gold Leaf Coil

To a coil with a metal material (in clinical test) which can be easily seen in CT (X-ray) images (for example, Ultra-Clip), were added 1.8 and of 0.44 M $HAuCl_4$, 3 g of CTAB, 2.5 g of butanol and 1.0 g of octane to gild a surface in order to obtain a gold leaf coil. [I-125]NaI 100 uCi was added to the gold leaf coil, and the resultant was reacted for 5 minutes at room temperature with stirring to construct a gold leaf coil to which a radioactive isotope was bound.

Example 5-2: Preparation of Gelatin Sponge 10 ml and of distilled water was add to 0.6 g of dried gelatin flake, and the resultant was heated at 60° C. until the gelatin was completely dissolved in order to obtain a gelatin solution. The gelatin solution was left at 4° C. for one hour to prepare gelatin. The prepared gelatin was heated at 160° C. for 3 hours to prepare gelatin sponge including a cross structure. The cross structure was formed by producing an isopeptide bond by reacting an amine group of a side chain of lysine and a carboxylic group of a side chain of glutamate or aspartate present in the gelatin at high temperature.

To investigate which material among the prepared gelatin and gelatin sponge shows in vivo stability, the gelatin and gelatin sponge were immersed in distilled water and left for 24 hours, as dissolubility thereof was measured (FIG. 12). FIG. 12 is an image showing a result of comparing dissolution levels of the gelatin and gelatin sponge with the lapse of time. As shown in FIG. 12, it has been found that gelatin having no cross-linking formed therein was completely dissolved in water within one day, while gelatin sponge having a cross-linking formed therein was not dissolved in water after one day.

Thus, it can be found that gelatin sponge, rather than gelatin, showed in vivo stability.

Example 5-3: Preparation of MAA-Based Solid-Type Labeling Agent by Using Gelatin Sponge and Evaluation of Availability Thereof A solid-type labeling agent was constructed by using the MAA constructed in Example 1, the radioactive isotope-bound gold leaf coil constructed in Example 5-1, the gelatin sponge constructed in Example 5-2, and ICG, and characteristics of a near-infrared fluorescent signal generated thereby was measured.

Example 5-3-1: Construction of Solid-Type Labeling Agent

The MAA constructed in Example 1 was mixed with 6.5, 65 or 650 µM of ICG. Then, the radioactive isotope-bound gold leaf coil constructed in Example 5-1 was added to the mixture to obtain a mixture. Gelatin was added to the mixture, and the resultant mixture was heated at 160° C. for 3 hours to prepare a solid-type labeling agent including the radioactive isotope-bound gold leaf coil ICG, MAA and gelatin sponge (Radiogoldcoil/EB-ICG-MAA-Gelatin sponge).

Each of the constructed solid-type labeling agent was immersed in distilled water, and left for one day, as intensity of near-infrared fluorescence was measured at immediately after immersion (0 hour), and 8 hours and 24 hours after immersion, and compared with those of the control (FIG. 13). As a control, ICG-Spongostan was prepared and used by mixing spongostan, which is one of conventionally available gelatin sponge, with 6.5, 65 or 650 μM of ICG solution. FIG. 13 is an image showing changes in intensity of near-infrared fluorescent signals of the control ICG-Spongostan and the solid-type labeling agent including the radioactive isotope-bound gold leaf coil, ICG, MAA and gelatin sponge with the lapse of time. As shown in FIG. 13, under the same ICG concentration, the solid-type labeling agent showed a relatively high level of intensity of a near-infrared fluorescent signal than the control. After 8 and 24 hours, ICG in the control was diffused, so that a near-infrared fluorescent signal was detected in distilled water per se, while an ICG diffusion rate of the solid-type labeling agent was in a low level.

Further, the solid-type labeling agents, which respectively includes different concentrations of ICGs, it can be found that the solid-type labeling agent including 650 μM of ICG showed the highest level of intensity of a near-infrared fluorescent signal.

Example 5-3-2: Comparison of ICG Diffusion Level and Intensity of Near-Infrared Fluorescent Signal in Mouse with Lapse of Time ICG-gelatin, ICG-Spongostan, and each solid-type labeling agent constructed by the method in the Examples by using ICGs having different concentrations from each other (6.5, 65 or 650 μM) were subcutaneously injected into nude mice. Each nude mouse was applied on the Xenogen Lumina device at immediate after injection (0 h), or one day (1 day), one week (1 week) or three weeks (3 week) after injection to measure intensity of near-infrared fluorescent signals exhibited at each injection site (FIG. 14). FIG. 14 is an image showing intensity of near-infrared fluorescent signals of the solid-type labeling agent, ICG-Spongostan and ICG-gelatin injected into the nude mice with the lapse of time. As shown in FIG. 14, for the solid-type labeling agent of the present invention, a near-infrared fluorescent signal was detected after 3 weeks, however, for ICG-Spongostan and ICG-gelatin, almost no near-infrared fluorescent signal was detected after 3 weeks. Also, when the solid-type labeling agent of the present invention was injected, it can be found that a high level of a near-infrared fluorescent signal was detected in the case where a high level of concentration of ICG was used during preparation of the solid-type labeling agent.

To sum up, it can be found that the complex of the present invention has an advantageous property as a labeling agent, because the complex remains in the injected lesion for long period of time, so that a rate of detecting micro lesion is high; and also accuracy of lesion excision is excellent due to strong signal.

INDUSTRIAL APPLICABILITY

The labeling composition for a cancer lesion of the present invention binds to a cancer lesion to make a size and site of the cancer lesion to be detected in real time during surgery, so that a success rate of a surgical operation of a cancer lesion is enhanced, and excess loss of normal tissues can be prevented. Therefore, the composition can be widely applied for effective anticancer therapy.

The invention claimed is:

1. A method for providing information about a size and a site of a cancer lesion, the method comprising:
   (a) adding a radioactive isotope to a thiol macroaggregated albumin (MAA) to obtain a complex in which the thiol MAA binds to the radioactive isotope;
   (b) adding at least one pigment for staining living tissues to the complex in (a);
   (c) mixing the complex in (b) with a first mixture comprising thrombine and aprotinin and a second mixture comprising fibrinogen and $CaCl_2$ to obtain the complex entangled in a fibrin;
   (d) administering directly to a cancer tissue to be removed in a subject the complex obtained from (c); and
   (e) identifying a size and a site of the cancer lesion through a signal selected from the group consisting of a color, a near-infrared fluorescence, a radioactivity, and a combination of two or more thereof, from the cancer tissue in real time during cancer-removing surgery.

2. The method of claim 1, wherein the pigment for staining living tissues is a visible pigment, or a fluorescent pigment.

3. The method of claim 2, wherein the visible pigment is selected from the group consisting of natural red, nile blue, bismark brown, lithium carmine, trypan blue, j anus green, methyl violet, o-lamine, malachite green, safranine, eosin, congo red, erythrocin, nigrosin, alcian blue hematoxylin, aniline blue, light green and a combination of two or more thereof.

4. The method of claim 2, wherein the fluorescent pigment is a near-infrared fluorescent pigment.

5. The method claim 4, wherein the near-infrared fluorescent pigment is an indocyanine green (ICG).

6. The method of claim 1, wherein the radioactive isotope is selected from the group consisting of H-3, C-14, P-32, S-35, Cl-36, Cr-51, Co-57, Co-58, Cu-64, Fe-59, Y-90, I-124, I-125, Re-186, I-131, Tc-99m, Mo-99, P-32, CR-51, Ca-45, Ca-68, and a combination of two or more thereof.

7. The method of claim 1, wherein the complex is captured inside of a gelatin or a gelatin sponge.

8. The method of claim 7, wherein the gelatin sponge is a construct in which an isopeptide bond is produced between an amine group of a side chain of lysine and a carboxylic group of a side chain of glutamate or aspartate present in the gelatin.

9. The method of claim 1, wherein the cancer is a solid cancer.

10. The method of claim 9, wherein the solid cancer is selected from the group consisting of prostate cancer, breast cancer, uterus cancer, skin cancer, cervical cancer, lung cancer, brain tumor, gastrointestinal tumor, liver cancer, soft tissue sarcoma, lymphoma, and a combination of two or more thereof.

11. A method for providing information about a size and a site of a cancer lesion, the method comprising:
   (a) adding at least one pigment for staining living tissues to a thiol macroaggregated albumin (MAA) to obtain a complex in which the thiol MAA binds to the pigment for staining living tissues;

(b) mixing the complex in (a) with a first mixture comprising thrombine and aprotinin and a second mixture comprising fibrinogen and $CaCl_2$ to obtain the complex entangled in a fibrin;

(c) mixing the complex in (b) with a gold leaf coil to which a radioactive isotope is bound;

(d) adding a gelatin to the mixture in (c) and then heating the resultant mixture to obtain a solid type labeling agent in which the mixture in (c) encaptured in a gelatin sponge;

(e) administering directly to a cancer tissue to be removed in a subject the solid type labeling agent obtained from (d); and (f) identifying the size and the site of the cancer lesion through a signal selected from the group consisting of a color, a near-infrared fluorescence, a radioactivity, and a combination of two or more thereof, from the cancer tissue in real time during cancer-removing surgery.

12. A kit for surgical removal of a cancer lesion comprising a labeling composition comprising a complex in which a macroaggregated albumin (MAA) is bound to a pigment for staining living tissues and a radioactive isotope, wherein the MAA is further bound to a fibrin, wherein the labeling composition is capable of being administered to a cancer tissue and the composition is capable of being used to identify a site and a size of a cancer lesion in real time during cancer-removing surgery.

13. A kit for surgical removal of a cancer lesion comprising a labeling composition comprising a complex in which a macroaggregated albumin (MAA) is bound to a pigment for staining living tissues and a radioactive isotope, wherein the MAA is further bound to a fibrin, wherein the labeling composition is capable of being administered to a cancer tissue and the composition is capable of being used to identify a site and a size of a cancer lesion in real time during cancer-removing surgery, and wherein the pigment for staining living tissues is a visible pigment, or a fluorescent pigment.

* * * * *